(12) United States Patent
Chiang et al.

(10) Patent No.: US 6,247,930 B1
(45) Date of Patent: *Jun. 19, 2001

(54) DISPOSABLE DENTAL TREATMENT TRAY FOR HOLDING MEDICAMENT GEL

(75) Inventors: Casper Chiang, Danville; Patrick J. Hanley, South San Francisco; Robert Perry, Freemont, all of CA (US)

(73) Assignee: Gillette Canada Company, Nova Scotia (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/408,252

(22) Filed: Sep. 29, 1999

(51) Int. Cl.[7] .................................................... A61G 17/02
(52) U.S. Cl. .............................................. 433/80; 433/215
(58) Field of Search ............................ 433/80, 215, 229, 433/6

(56) References Cited

U.S. PATENT DOCUMENTS

| 273,893 | 5/1984 | Weitzman . |
| 0,955,281 | 5/1976 | Weitzman . |
| 4,044,762 | 8/1977 | Jacobs . |
| 4,064,628 | 12/1977 | Weitzman . |
| 4,138,814 | 2/1979 | Weitzman . |
| 4,173,219 | 11/1979 | Lentine . |
| 4,173,505 | 11/1979 | Jacobs . |
| 4,376,628 | 3/1983 | Aardse . |
| 4,428,373 | * 1/1984 | Seid et al. ........................ 433/80 X |
| 4,544,354 | 10/1985 | Gores et al. . |
| 4,560,351 | 12/1985 | Osborne . |
| 4,902,227 | 2/1990 | Smith . |
| 5,211,559 | 5/1993 | Hart et al. . |
| 5,297,960 | 3/1994 | Burns . |
| 5,336,086 | 8/1994 | Simmen et al. . |
| 5,460,527 | * 10/1995 | Kittlesen ........................... 433/215 |
| 5,759,037 | 6/1998 | Fischer . |
| 5,846,058 | 12/1998 | Fischer . |
| 5,895,218 | 4/1999 | Quina et al. . |

* cited by examiner

Primary Examiner—Nicholas D. Lucchesi
(74) Attorney, Agent, or Firm—David A. Howley

(57) ABSTRACT

The present invention relates to a tray for holding medicament to be applied to the teeth and gums of a patient, said tray being unitarily formed of a flexible composite material comprising a flexible, fine-celled polymeric foam upper layer, a tying layer and a film bottom layer. Said tray provides the user with a comfortable fit and exhibits improved mechanical and chemical resistance characteristics. Said trays are stable, even when decorated with ornamental printing.

18 Claims, 3 Drawing Sheets

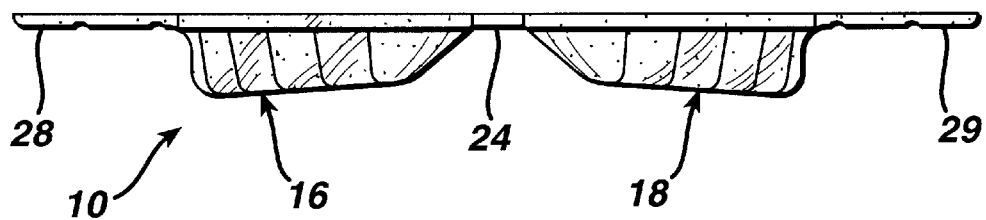
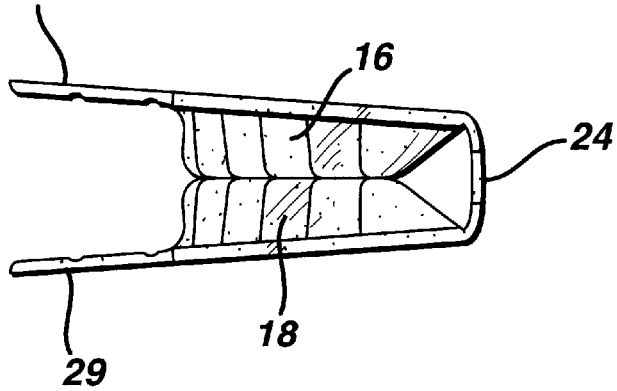
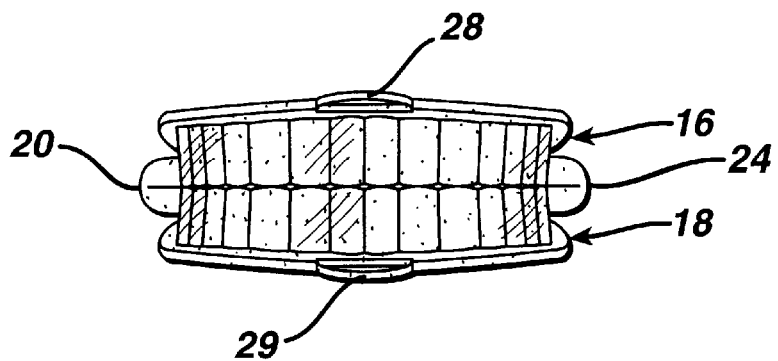

DISPOSABLE DENTAL TREATMENT TRAY FOR HOLDING MEDICAMENT GEL

FIELD OF THE INVENTION

This invention is directed to a dental treatment tray and a combination of the tray with a medicament gel filling to be applied to the teeth and gums of a patient. More particularly, the present invention is directed to an improved dental treatment tray suitable for holding a gel containing a medicament such as a fluoride compound to be applied to the teeth and gums of a patient.

BACKGROUND OF THE INVENTION

It is often necessary for a fluoride containing gel or a gel containing another medicament to be applied to the teeth and gums of dental patients. For this purpose, it has been known to form a tray for the application of such a gel. Typically, these trays are disposable and are molded from a closed-cell polyethylene foam. An example of a conventional disposable tray is that sold by Oral-B Laboratories consisting of a unitary tray structure having upper and lower cups as depicted in US. Pat. Nos. Des. 273,893 and 5,211,559, incorporated herein by reference. Each of the cups has a shape which roughly conforms to the upper or lower teeth, i.e., a generally C-shape, and has a concave medicament receiving surface. The cups are secured together by hinge straps which normally maintain the cups in a planar relationship with both medicament receiving surfaces facing in the same direction. A gel is then loaded into the medicament receiving surfaces from a container such as a tube, after which the tray is folded about the hinge straps so that the cups overlie one another with the medicament receiving surfaces facing away from one another. The tray, in this folded state, is then inserted into the patient's mouth. The patient then bites down firmly into the concave medicament receiving surfaces and holds that position until the treatment is completed, after which the unit is removed from the patient's mouth and discarded.

It is important that disposable trays are fabricated from a soft, compliant material to provide a comfortable fit to the user. Early disposable trays were fabricated from a hard vinyl material which met with great complaints. It is also important that these disposable trays also maintain mechanical and chemical integrity during use. For example, disposable foam trays as described above have a tendency to warp and deform during use. This warping can cause the treatment gel to spill or leak from the tray. Furthermore, the hinge element of the tray can sometimes structurally fail, resulting in a very uncomfortable fit for the user. Still further, it is difficult to provide printed ornamentation and labeling on such tray, due to the fact that a wide number of medicament gels must are used in such trays; these medicament pose chemical compatibility concerns. Heretofor, these shortcomings have not been solved Therefore, it is an object of the present invention to provide a disposable dental treatment tray for holding medicament gels which solves these problems.

U.S. Pat. Nos. 4,173,219, 4,376,628, 4,428,373, 5,211,559, and Des. 273,893 discloses a disposable dental tray configurations which can be adapted to the present invention, all incorporated in their entirety by reference.

Treatment gels and foamable solutions containing fluorides and other medicaments, formulated and packaged for filling and application to the teeth and gums of a patient in a dental treatment tray by a dentist are well known. Particularly suited for use in the present invention are the fluoride foam medicated gels described in U.S. Pat. Nos. 4,770,634, 5,071,637 and 5,073,363, incorporated herein by reference.

SUMMARY OF THE INVENTION

The present invention relates to a tray for holding medicament to be applied to the teeth and gums of a patient, said tray being unitarily formed of a flexible composite material comprising a flexible, hydrophobic, fine-celled polymeric foam upper layer, a tying layer and a film bottom layer.

It is an object of the present invention to provide a tray for holding a medicament to be applied to the teeth and gums of a patient, which tray provides the user with a comfortable fit and exhibits improved mechanical and chemical resistance characteristics. Said trays are stable, even when decorated with ornamental printing.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 3 is a left side plan view of an unloaded tray according to the embodiment of FIG. 1 in an unfolded state, wherein said right side plan view is a mirror image thereof;

FIG. 4 is a side view of an unloaded tray according to the embodiment of FIG. 1 in a folded state;

FIG. 5 is a front view of an unloaded tray according to the embodiment of FIG. 2 in a folded state;

DESCRIPTION OF THE PREFERRED EMBODIMENTS

Figure 1:
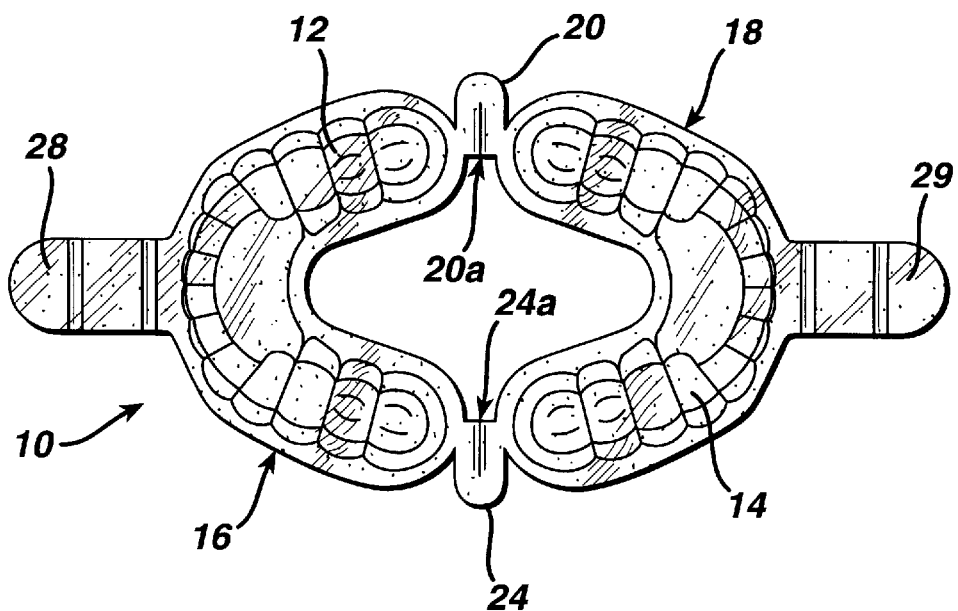
FIG. 1 is a bottom plan view of an unloaded tray according to an embodiment of the present invention in an unfolded state.

Embodiments of the present invention will now be described with reference to the attached figures, wherein the same or corresponding reference numerals will be used to identify the same or corresponding parts throughout the several views.

The tray according to the present invention is unitarily formed of composite material 1. Referring to FIG. 8, the composite material comprises a flexible, fine-celled polymeric foam upper layer 2, a tying layer 3, and a film bottom layer 4. Said composite 1 is readily moldable to the desired configuration and which is of relatively inexpensive construction so as to warrant its economic disposal after a single use. It is desirable to fabricate the tray of hydrophobic materials. (See U.S. Pat. No. 4,173,505, incorporated herein by reference, for a typical foam tray manufacturing. The present manufacturing operation can readily be adapted therefrom by one of ordinary skill in the art) Furthermore, the resulting dental tray (See FIGS. 1–7) is sufficiently strong so as to resist warping and is tough enough to prevent bite through by the user and/or hinge failure.

The flexible, fine-celled polymeric foam upper layer material 2 may be any orally safe material which is inert to medicaments and saliva. Preferably said materials are closed cell foams. Most preferably, said flexible, hydrophobic, fine-celled polymeric foam upper layer material 2 is selected from the group consisting of polyethylene, polyurethane, cellulosic polymers, polystyrene, polyvinyl chloride and combinations thereof. Polyethylene being the most desirable.

The film bottom layer 4 may be any orally safe material which is inert to medicaments and saliva. Preferably said materials are hydrophobic barrier films. Most preferably, said film bottom layer 4 material is selected from the group consisting of polyethylene, polyurethane, poly(ethylene terephthalate), polypropylene, nylon, poly(vinyl chloride), any man made clear film and combinations thereof. Polyethylene being the most desirable.

Figure 10:
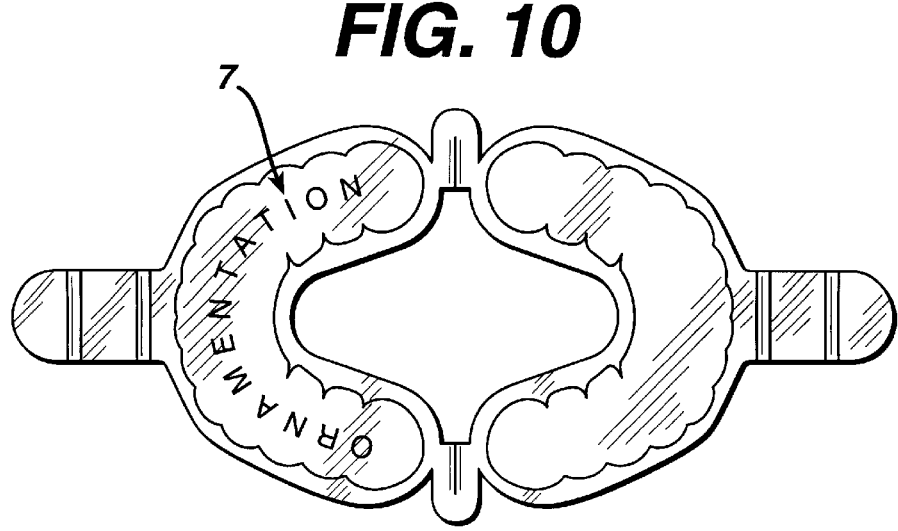
FIG. 10 is a bottom plan view of a tray according to the embodiment of FIG. 1 with ornamental printing thereon.

The tying layer 3 serves two purposes. First, it acts as a compatiblizer for the upper and bottom layers and second, it provides another film layer onto which ornamentation may be added to the tray. By placing ornamentation on or within the tying layer it is protected from the medicament and saliva, both of which might have a solvency toward the inks, dyes and pigments used in the ornamentation. FIG. 10 depicts an embodiment of the present invention with ornamentation 7. It is important to note that the bottom layer 4 should be at least translucent, and preferably transparent in order to allow the printed ornamentation on tying layer to show through to the user. Preferably, the tying layer must be thermally (i.e. moldably) compatible with the upper 2 and bottom materials 4. In situations where the materials are not totally compatible an additional adhesive layer may be employed.

The tying bottom layer material 3 may be any orally safe material which is inert to medicaments and saliva. Preferably, said tying layer material 3 is selected from the group consisting of polyethylene, polyurethane, Polyethylene, polyurethane, cellulosic polymers, polyvinyl chloride, polystyrene, polypropylene, nylon, poly (ethylene, terephthalate) and combinations thereof. Anhydrous polypropylene and anhydrous polyethylene being the most desirable.

Figure 9:
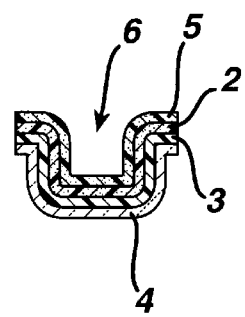
FIG. 9 is an 8—8 sectional view of the tray according to FIG. 8 depicting a second embodiment of the present invention.

Referring to FIG. 9, in a second embodiment of the present invention, the tray further comprises an open cell foamed material 5 affixed to the upper medicament receiving surface 6 of said flexible, hydrophobic fine-celled polymeric foam material. Said open cell foamed material 5 should be inert to medicaments. It is selected from the group consisting of polyethylene, polyurethane, cellulosic polymers, polystyrene, polyvinyl chloride and combinations thereof. Most preferably, said open cell foamed material is polyethylene. It may be affixed to the upper medicament receiving surface 6 via a thermal bond achieved during a foaming operation or during a subsequent welding operation or, alternatively, it may be adhesively bonded with any adhesive with is Generally Regarded AS Safe (GRAS) for oral applications.

Figure 2:
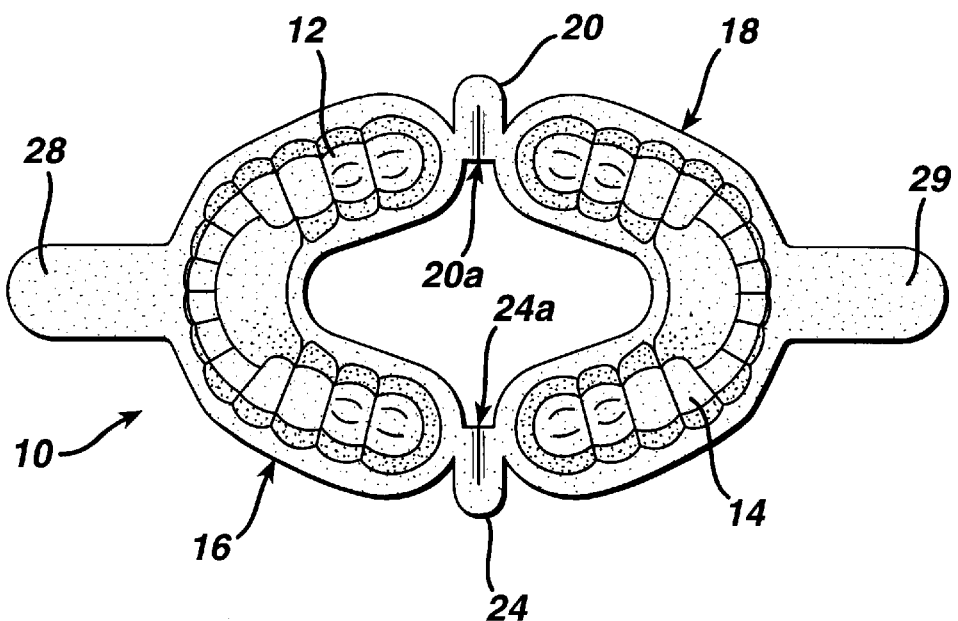
FIG. 2 is a top plan view of an unloaded tray according to the embodiment of FIG. 1 in an unfolded state.

Referring to FIGS. 1 and 2, the tray 10 according to the invention has a generally C-shaped cup portion 16 and a generally C-shaped cup portion 18, each of which is concaved to define first and second concave medicament receiving surfaces 12 and 14.

It should be noted that the cup portions 16 and 18 are generally C-shaped only insofar as this shape generally conforms to the arrangement of upper and lower teeth in a patient's jaw. Various other shapes which also generally conform to the arrangement of teeth in a patient's jaw are therefore also included within the reference to the shape of the cup portions being generally C-shaped.

The facing ends of the cup portions are flexibly united by hinge straps 20 and 24 such that the cup portions 16 and 18 normally lie in a plane. The hinge straps 20 and 24 have hinge creases 20a and 24a to increase their flexibility.

The mid-portions of the cup portions 16 and 18 are provided with unitary handles 28 and 29 which extends therefrom in a direction opposite to the cup portions 18 and 16 respectively.

Figure 6:
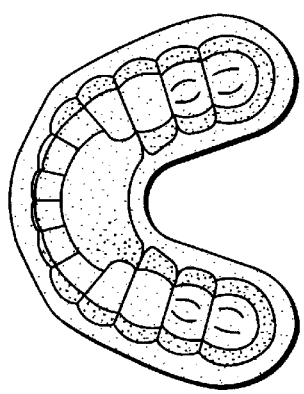
FIG. 6 is a top plan view of a single cavity unloaded tray according to the present invention.
Figure 7:
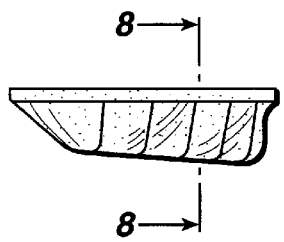
FIG. 7 is a left side view of an unloaded tray according to the embodiment of FIG. 6 wherein the right side view is a mirror image thereof.
Figure 8:
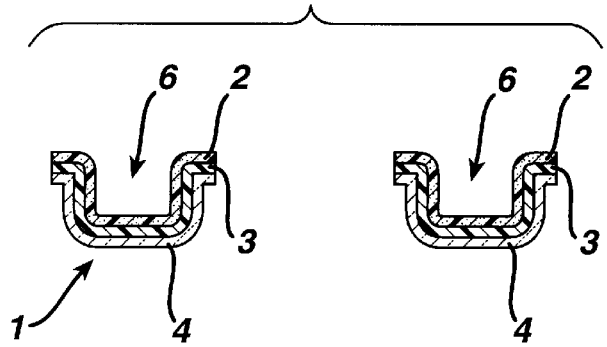
FIG. 8 is an 8—8 sectional view of the tray according to FIG. 7.

FIGS. 6 and 7 show another embodiment which is identical to the first embodiment, except that only on C-shaped cup portion 16 is used.

The tray is designed to be loaded with a dental treatment agent in a suitable vehicle such as a gel for application to the teeth and gums of a patient. Optionally, the disposable tray can be provided to the dentist already loaded with the treatment gel to be applied. The terms "loaded" and "preloaded", as used herein, are defined to mean that some portion of the treatment agent has been placed in the trough formed by the tray's foam interior. Preferably, the amount of treatment agent loaded in the tray corresponds to the full amount which the dentist wishes to use in the dental tray treatment method.

The medicinal treatment agent contains a medicament or treatment agent for treating teeth or gums in the form of a coating, gel, paste, solution or the like. The gel, paste or solution forms of treatment agent can be applied to the brush by the dentist or it can be provided to the dentist in the preloaded form.

Medicament coatings, solutions, pastes and gels are well known and fully within the skill of the art. The preferred medicament vehicle is a gel medium. Treatment gels which are suitable for use with and for preloading the dental treatment tray of this invention are well known and fully within the skill of the art. In general, the gels comprise an aqueous solution of the medicament and pharmaceutically acceptable, non-toxic additives such as aqueous gelling agents, humectants, surfactants, coloring or whitening agents, chlorophyll compounds, flavoring agents, preservatives, optional co-solvents, stabilizers, sweeteners, dyes, and pH modifying agents. Suitable materials and manufacturing processes are described in U.S. Pat. Nos. 4,418,057, 4,254,101, 4,627,977, 4,806,340, 4,847,070, 4,902,497, 4,906,456, and 4,960,586, for example, the entire contents of each of which are incorporated by reference.

Suitable medicaments include antimicrobial treatment agents. Suitable antimicrobial agents include, but are not limited to, quaternary ammonium compounds such as cetylpyridinium chloride, domiphen bromide, benzethonium chloride and the like; antibiotics and related drugs such as nitroimidazoles (metronidazole, etc.), tetracyclines, penicillins, clindamycin, spiramycin, nystatin, amphotericin, erythromycin, and the like; essential oils such as thymol, eucalyptol, menthol, methyl salicylate, and the like; metal salts such as mercurials, zinc salts, aluminum salts, and the like; other treatment compounds such as chlorhexidine, alexidine, hexetridine, IRGASAN DP300, salicylanilides, and the like.

Suitable flavors and fragrances include organic acids, esters, and aldehydes which are both safe and pleasant. Any suitable flavoring or sweetening material may also be employed. Examples of suitable flavoring constituents are flavoring oils, e.g. oil of spearmint, peppermint, wintergreen, sassafras, clove, save, eucalyptus, marjoram, cinnamon, lemon, orange and methyl salicylate. Suitable sweetening agents include sucrose, lactose, maltose, dextrose, levulose, sorbitol, xylitol, d-tryptophan, dihydrochalcones, sodium cyclamate, perillartine, APM (aspartyl phenyl alanine, methyl ester), saccharine and the like.

Biologically active materials which can be included in the gels are growth hormones and other compounds or compositions which enhance or stimulate tissue regrowth and healing.

Oxygenating agents which can be included in the gels include sodium perborate, urea peroxide, stabilized hydrogen peroxide, and the like.

Fluorides which can be included in the gels include sodium fluoride, stabilized stannous fluoride, amine fluorides and the like. A suitable stabilized stannous fluoride treatment gel is disclosed in U.S. Pat. Nos. 4,960,586 and 5,009,883, for example, the entire contents of which are hereby incorporated by reference. The fluoride can be provided in concentrations of from 0.05 to 5.0 weight percent.

Desensitizing agents which can be included in the gels include hydroxyapatite, formaldehyde, soluble oxalates, potassium salts include potassium fluoride, and the like.

Any other soluble, non-toxic pharmaceutically acceptable material which has a beneficial or therapeutic effect on the health, integrity or appearance of oral hard and soft tissues can be incorporated in the gels.

Any conventional humectant can be used. Suitable humectants include sorbitol, glycerin, or other edible polyhydric alcohols, the natural or synthetic gums conventionally used as hardening control agents and binders.

Suitable gelling agents for use in the composition of this invention include from 0.1 to 10 and preferably from 0.5 to 5 weight percent gelling agent. Gelling agents should be colloidal silica, magnesium aluminum silicate, and silicate free compounds such as Irish moss, gum karaya, gum arabic, gum tragacanth, xanthan gum, other polysaccharide gums, starch, polyvinylpyrrolidone, hydroxyethyl propylcellulose, hydroxybutyl methyl cellulose, hydroxypropyl methyl cellulose, hydroxyethyl cellulose, sodium carboxymethyl cellulose, other hydroxyvinyl polymers, and the like.

The compositions should have a pH within the range of from 2 to 11. One embodiment of treatment gel for treating intact teeth has an acidic pH and contains hydrofluoric and phosphoric acids. A neutral treatment gel is preferred to treat teeth for which acid treatment is not suitable.

An optimum acidic gel can have the following approximate composition:

| Component | Amount, % w/w |
|---|---|
| Gelling agemt | 2.5 |
| Glycerin | 5.0 |
| Aqueous Hydrofluoric Acid | 0.2 |
| Aqueous Phosphoric Acid | 1.5 |
| Sodium Fluoride | 2.6 |
| Sorbitol solution | 45.0 |
| Water | 41.0 |
| Xanthan Gum | 0.4 |

An optimum neutral gel can have the following composition:

| Component | Amount, % w/w |
|---|---|
| Gelling agent | 1.8 |
| Sodium Fluoride | 1.9 |
| Sodium Hydroxide Solution | 9.0 |
| Sorbitol Solution | 20.0 |
| Water | 65.2 |

This invention is further illustrated by the following specific but non-limiting examples of suitable gels which can be applied to the dental treatment tray of this invention.

EXAMPLE 1

Acidic Minute Treatment Gel

The following ingredients are combined to produce an acidic Minute Treatment Gel used for fluoride treatment of teeth.

| Component | Amount, % w/w |
|---|---|
| Carbopol sup a | 2.500 |
| FD & C Yellow #10 (1.0% aq. solution) | 0.085 |
| FD & C Blue #1 (1.0% aq. solution) | 0.025 |
| Glycerin 96% USP | 5.000 |
| Hydrofluoric Acid, 48% AR | 0.174 |
| Phosphoric Acid 75%, Food Grade | 1.490 |
| Prosweet Liquid sup b | 1.000 |
| Sodium Fluoride, USP | 2.599 |
| Sodium Saccharin USP Crystals | 0.210 |
| Sorbitol 70.0% Solution USP | 45.000 |
| Spearmint Oil NF, Extra | 0.600 |
| Titanium Dioxide USP | 0.010 |
| Water, Purified USP | 40.927 |
| Xanthan Gum sup c | 0.380 | sup a CARBOMER 934P NF, carboxyvinyl polymer
sup b F & C International
sup c KELTROL, Kelco

EXAMPLE 2

Neutral Treatment Gel

The following ingredients are combined to produce an Neutral Treatment Gel used for fluoride treatment of teeth.

| Component | Amount, % w/w |
|---|---|
| Carbopol 934P sup a | 1.800 |
| FD & C Blue #1 (1.0% Solution) | 0.054 |
| FD & C Red #33 (1.0% Solution) | 0.123 |
| Grape Flavor #11540 sup b | 0.500 |
| Methylparaben NF | 0.150 |
| Propylparaben NF | 0.050 |
| Prosweet Liquid sup c | 1.000 |
| Sodium Fluoride, USP | 1.870 |
| Sodium Hydroxide (10% Solution) | 9.000 |
| Sodium Saccharin USP Crystals | 0.210 |
| Sorbitol Solution 70% USP | 20.000 |
| Titanium Dioxide USP | 0.010 |
| Water, Purified USP | 65.233 | sup a CARBOMER 934P NF, carboxyvinyl polymer
sup b Bush, Boake & Allen
sup c F & C International Obviously, numerous modifications and variations of the present invention are possible in light of the above teachings. It is therefore to be understood that within the scope of the appended claims, the invention may be practiced otherwise than as specifically described herein.

The invention claimed is:

1. A tray for holding medicament to be applied to the teeth and gums of a patient, said tray being unitarily formed of a flexible composite material comprising a flexible hydrophobic, fine-celled polymeric foam upper layer, a tying layer and a film hydrophobic bottom layer.

2. A tray according to claim 1 where in said tray comprises: a generally C-shaped cup portion defining a concave medicament receiving surface.

3. A tray according to claim 1 wherein said tray comprises:

a generally C-shaped cup portion defining a first concave medicament receiving surface;

a second generally C-shaped cup portion defining a second concave medicament receiving surface;

hinge straps flexibly uniting said first and second cup portions such that said first and second cup portions normally lie substantially in a plane with ends of said first generally C-shaped cup portion facing respective ends of said second generally C-shaped cup portion, and such that said first and second concave surfaces open in the same direction; and a handle extending from both of said cup portions in a direction away from the other of said cup portions whereby said tray may be folded about said hinge straps such that said cup portions overlie one another with said medicament receiving surfaces facing away from one another.

4. A tray according to claim 3 wherein said flexible, hydrophobic, fine-celled polymeric foam upper layer material is selected from the group consisting of polyethylene, polyurethane, cellulosic polymers, polystyrene, polyvinyl chloride and combinations thereof.

5. A tray according to claim 4 wherein said flexible, fine-celled polymeric foam material is polyethylene.

6. A tray according to claim 4 wherein said tying layer material is selected from the group consisting of polyethylene, polyurethane, cellulosic polymers, polyvinyl chloride, polystyrene, polypropylene, nylon, poly(ethylene terephthalate) and combinations thereof.

7. A tray according to claim 6 wherein said tying layer material is anhydrous polyethylene or anhydrous polypropylene.

8. A tray according to claim 6 wherein said hydrophobic film bottom layer material is selected from the group consisting of polyethylene, polyurethane, poly(ethylene terephthalate), polypropylene, nylon, poly(vinyl chloride), any man made clear film, and combinations thereof.

9. A tray according to claim 8 wherein said hydrophobic film bottom layer material is polyethylene.

10. A tray according to claim 9 wherein said hydrophobic film bottom layer is transparent.

11. A tray according to claim 10 wherein said tying layer material has bottom-side ornamentation printed thereon.

12. A tray of claim 11 wherein the treatment gel has an acidic pH and contains pharmaceutically acceptable, treatment effective amounts of phosphoric acid and hydrofluoric acid.

13. A tray of claim 10 wherein the treatment gel contains from 0.05 to 5 wt. % of a soluble fluoride.

14. A tray according to claim 9 wherein said hydrophobic film bottom layer has bottom-side ornamentation printed thereon.

15. A tray according to claim 2 further comprising an open cell foamed material affixed to the upper medicament receiving surface of said flexible, hydrophobic fine-celled polymeric foam material.

16. A tray of claim 2, wherein said tray is sufficiently stiff material to maintain said tray substantially rigid when in said folded state with groove held in said narrow space and is sufficiently strong so as to resist warping and is inert to said medicament.

17. A tray of claim 2 in combination with a treatment agent comprising a pharmaceutical effective amount of at least one agent for treating gums or teeth in a non-toxic, pharmaceutically acceptable vehicle.

18. A tray of claim 17 in combination with a treatment gel comprising a pharmaceutically effective amount of at least one agent for treating teeth or gums dispersed in a gel medium consisting essentially of water and an amount of a water dispersible gelling agent sufficient to form a gel.

* * * * *